(12) United States Patent
Shi et al.

(10) Patent No.: US 8,685,728 B2
(45) Date of Patent: Apr. 1, 2014

(54) KIT CONTAINING STEM CELLS AND CYTOKINES FOR USE IN ATTENUATING IMMUNE RESPONSES

(75) Inventors: Yufang Shi, Belle Mead, NJ (US); Guangwen Ren, Piscataway, NJ (US); Liying Zhang, Belle Mead, NJ (US)

(73) Assignee: Rutgers The State University of New Jersey, New Brunswick, NJ (US)

( * ) Notice: Subject to any disclaimer, the term of this patent is extended or adjusted under 35 U.S.C. 154(b) by 60 days.

(21) Appl. No.: 12/362,847

(22) Filed: Jan. 30, 2009

(65) Prior Publication Data
US 2009/0202479 A1 Aug. 13, 2009

Related U.S. Application Data

(60) Provisional application No. 61/063,288, filed on Jan. 31, 2008.

(51) Int. Cl.
*C12N 5/0775* (2010.01)
*C07K 14/52* (2006.01)

(52) U.S. Cl.
USPC .................. 435/372; 530/351; 514/885

(58) Field of Classification Search
None
See application file for complete search history.

(56) References Cited

U.S. PATENT DOCUMENTS

| | | | |
|---|---|---|---|
| 5,741,815 A | 4/1998 | Lai | 514/492 |
| 5,847,004 A | 12/1998 | Lai | 514/599 |
| 5,849,282 A | 12/1998 | Kawai et al. | 424/85.1 |
| 5,942,225 A * | 8/1999 | Bruder et al. | 424/93.7 |
| 2005/0233443 A1* | 10/2005 | Freyman | 435/343 |
| 2007/0128722 A1 | 6/2007 | Lin et al. | 435/366 |
| 2007/0160583 A1 | 7/2007 | Lange et al. | 424/93.7 |

OTHER PUBLICATIONS

Ren et al (2008. Cell Stem Cell. 2: 141-150).*
Keating et al, 2008. Cell Stem Cell. 2: 106-107.*
Rifas (2006. Journal of Cellular Biochemistry. 98: 706-714).*
Dulbecco's Modified Eagle's Medium Product No. D5523 (Product Data Sheet), Sigma-Aldrich, 1 page, Apr. 2007.*
Cheng et al (1994. Endocrinology. 134(1): 277-286).*
Aggarwal et al., "Human mesenchymal stem cells modulate allogeneic immune cell responses", Blood 2005 105(4):1815-1822.
Dazzi et al., "The role of mesenchymal stem cells in haemopoiesis", Blood Reviews 2006 20:161-171.
Denham et al., "Inhibition of the reactive proliferation of lymphocytes by activated macrophages:the role of nitric oxide", Clin. Exp. Immunol. 1992 87:157-162.
Djouad et al., "Reversal of the immunosuppressive properties of mesenchymal stem cells by tumor necrosis factor α in collagen-induced arthritis", Arthritis & Rheumatism 2005 52(5):1595-1603.
Hattori et al., "Differential effects of anti-fas ligand and anti-tumor necrosis factor α antibodies on acute graft-versus-host disease pathologies", Blood 1998 91(11):4051-4055.
Inoue et al., "Immunomodulatory effects of mesenchymal stem cells in a rat organ transplant model", Transplantation 2006b 81(11):1589-1595.
Isobe et al., "Nitric oxide production from a macrophage cell line:interaction with autologous and allogeneic lymphocytes", Journal of Cellular Biochemistry 1993 53:198-205.
Keating, Armand, "Mesenchymal stromal cells", Current Opinion in Hematology 2006 13:419-425.
Koc et al., "Mesenchymal stem cells-Allogeneic mesenchymal stem cell infusion for treatment of metachromatic leukodystrophy (MLD) and Hurler syndrome (MPS-IH)", Bone Marrow Transplantation 2002 30;215-222.
Krampera et al., "Role for interferon-γ in the immunomodulatory activity of human bone marrow mesenchymal stem cells", Stem Cells 2006 24:386-398.
Le Blanc et al., "Treatment of severe acute graft-versus-host disease with third party haploidentical mesenchymal stem cells", The Lancet 2004 363:1439-1441.
Le Blanc et al., "Mesenchymal stem cells:properties and role in clinical bone marrow transplantation", Current Opinion in Immunology 2006 18:586-591.
Meisel et al., "Human bone marrow stromal cells inhibit allogeneic T-cell responses by indoleamine 2,3-dioxygenase-mediated tryptophan degradation", Blood 2004 103(12):4619-4621.
McCarthy, Jr., et al., "Inhibition of interleukin-1 by an interleukin-1 receptor antagonist prevents graft-versus-host disease", Blood 1991 78(8):1915-1918.
Miszta-Lane et al., Stem cell sources for clinical islet transplantation in type 1 diabetes:embryonic and adult stem cells, Medical Hypotheses 2006 67:909-913.
Plumas et al., "Mesenchymal stem cells induce apoptosis of activated T cells", Leukemia 2005 19:1597-1604.
Rasmusson et al., "Mesenchymal stem cells inhibit lymphocyte proliferation by mitogens and alloantigens by different mechanisms", Experimental Cell Research 2005 305:33-41.
Sato et al., "Nitric oxide plays a critical role in suppression of T-cell proliferation by mesenchymal stem cells", Blood 2007 109(1):228-234.
Schenk et al., "Monocyte chemotactic protein-3 is a myocardial mesenchymal stem cell homing factor", Stem Cells 2007 25:245-251.
Uccelli et al., "Immunoregulatory function of mesenchymal stem cells", Eur. J. Immunol. 2006 36:2566-2573.
van Laar et al., "Adult stem cells in the treatment of autoimmune diseases", Rheumatology 2006 45:1187-1193.
Xu et al., "Immunosuppressive properties of cloned bone marrow mesenchymal stem cells", Cell Research 2007 17:240-248.
Zappla et al., "Mesenchymal stem cells ameliorate experimental autoimmune encephalomyelitis inducing T-cell anergy", Blood 2005 106(5):1755-1761.

* cited by examiner

*Primary Examiner* — Zachary Howard
(74) *Attorney, Agent, or Firm* — Fox Rothschild LLP

(57) ABSTRACT

The present invention relates to a composition and methods of treatment for inflammation comprising of adult stem cells and inflammatory cytokines. The invention further relates to the treatment of inflammation associated with autoimmune disorders, allergies, sepsis, cancer as well as to preventing, reducing or treating transplant rejection and/or graft-versus-host disease (GvHD).

5 Claims, 3 Drawing Sheets

SEQUENCE LISTING

<160> NUMBER OF SEQ ID NOS: 2

<210> SEQ ID NO 1
<211> LENGTH: 21
<212> TYPE: DNA

```
<213> ORGANISM: Artificial sequence
<220> FEATURE:
<223> OTHER INFORMATION: Synthetic oligonucleotide

<400> SEQUENCE: 1
cagctgggct gtacaaacct t                                              21

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 2
cattggaagt gaagcgtttc g                                              21
```

KIT CONTAINING STEM CELLS AND CYTOKINES FOR USE IN ATTENUATING IMMUNE RESPONSES

INTRODUCTION

This application claims benefit of priority from U.S. Provisional Patent Application Ser. No. 61/063,288, filed Jan. 31, 2008, the content of which is incorporated herein by reference in its entirety.

This invention was made in the course of research sponsored by the National Space Biomedical Research Institute (IIH00405), which is supported by the National Aeronautics and Space Administration through the Cooperative Agreement NCC 9-58. The U.S. government has certain rights in this invention.

BACKGROUND OF THE INVENTION

Stem cells have two distinct characteristics that distinguish them from other cell types. First, they are unspecialized and can self-renew for long periods without significant changes in their general properties. Second, under certain physiologic or experimental conditions, stem cells can be induced to differentiate into various specialized cell types. Thus, stem cells hold a great promise for regenerative medicine. There are two major types of stem cells: embryonic stem (ES) cells and adult stem cells. Adult stem cells exist in many mature tissues, such as bone marrow, muscle, fat and brain. While most studies of adult stem cells have focused on $CD34^+$ hematopoietic stem cells, the distinct lineage of $CD34^-$ fibroblast-like mesenchymal stem cells (MSCs), especially those derived from bone marrow, have attracted significant attention from basic and clinical investigators (Chen, et al. (2006) *Immunol. Cell Biol.* 84:413-421; Keating (2006) *Curr. Opin. Hematol.* 13:419-425; Pommey & Galipeau (2006) *Bull. Cancer* 93:901-907). Bone marrow-derived MSCs have been shown to differentiate into several different types of tissue, such as cartilage, bone, muscle, and adipose tissue (Barry & Murphy (2004) *Int. J. Biochem. Cell Biol.* 36:568-584; Le Blanc & Ringden (2006) *Lancet* 363:1439-1441).

The promise of ES cells in regenerative medicine is extremely exciting; yet, research has not focused on the possible immunological conflict between ES cell-regenerated tissues, which are almost always allogeneic in nature, and the recipient hosts (Bradley, et al. (2002) *Nat. Rev. Immunol.* 2(11):859-71). There is clear evidence that immunological rejection of transplanted fetal and ES cell-derived tissues occurs very frequently (Aggarwal & Pittenger (2005) *Blood* 105:1815-1822; Drukker (2004) *Springer Semin. Immunopathol.* 26(1-2):201-13; Drukker & Benvenisty (2004) *Trends Biotechnol.* 22(3):136-41). On the other hand, unlike ES cells, MSCs can be highly immunosuppressive. In some studies, MSCs were found to suppress proliferation and cytokine production by T cells stimulated with mitogen or antigen (Dazzi, et al. (2006) *Blood Rev.* 20:161-171; Keating (2006) supra; Schenk, et al. (2006) *Stem Cells* 25:245-251; van Laar & Tyndall (2006) *Rheumatology* (Oxford) 45:1187-1193). MSCs have also been used to promote the engraftment of transplanted bone marrow and potentially ES cells (Le Blanc & Ringden (2006) *Curr. Opin. Immunol.* 18:586-591; Miszta-Lane, et al. (2006) *Med. Hypotheses* 67:909-913). In another study, no evidence of alloreactive T cells and no incidence of graft-versus-host disease (GVHD) were found when as few as $2\times10^6$ allogeneic MSCs per kg were infused along with allogeneic bone marrow into patients with metachromatic leukodystrophy, or Hurler's syndrome (Koc, et al. (2002) *Bone Marrow Transplant* 30:215-222). Several groups have attempted to use MSCs to prevent or treat autoimmune diseases, such as experimental autoimmune encephalomyelitis induced by MOG35-55 in C57BL/6J mice (Zappia, et al. (2005) *Blood* 106:1755-1761) and collagen-induced arthritis (Djouad, et al. (2005) *Arthritis Rheum.* 52:1595-1603). Interestingly, the immunomodulatory effect of MSCs is not always achieved (Djouad, et al. (2005) supra; Inoue, et al. (2006) *Transplantation* 81:1589-1595; Nauta, et al. (2006) *Blood* 108:2114-2120).

Elucidation of the mechanisms through which MSCs suppress immune reactions would offer better utility of these cells. In this regard, immunosuppression by MSCs has been demonstrated to involve IL-10 (Batten, et al. (2006) *Tissue Eng.* 12:2263-2273), TGF-β (Groh, et al. (2005) *Exp. Hematol.* 33:928-934), nitric oxide (Sato, et al. (2007) *Blood* 109:228-234), indoleamine 2,3-dioxygenase (IDO) (Meisel, et al. (2004) *Blood* 103(12):4619-21), and prostaglandin (PG) E2 (Aggarwal & Pittenger (2005) supra).

Nitric oxide (NO) is a rapidly diffusing gaseous molecule that is bioactive (Stamler, et al. (1992) *Science* 258:1898-1902). It is a free radical with one unpaired electron and is capable of affecting a diverse range of biological activities in both animals and plants.

The human and mouse genomes contain genes encoding three different NO synthases: iNOS, found in macrophages and other cell types; nNOS, found in neurons; and eNOS, found in endothelial cells. The levels of nNOS and eNOS are relatively steady, while iNOS expression is inducible and plays a major role in immune regulation. With regard to the role of NO in the immune system, besides its well established role in macrophages, recently NO has been shown to affect TCR signaling, cytokine receptor expression, and the phenotypes of T cells (Niedbala, et al. (2006) *Ann. Rheum. Dis.* 65 Suppl 3:iii37-iii40).

Chemokines are a superfamily of secreted small proteins that mediate leukocyte trafficking, recruitment, and recirculation during many pathophysiological processes. Chemokines are divided into subfamilies based on their conserved amino acid sequence motifs. Most chemokines have at least four conserved cysteine residues that form two intramolecular disulfide bonds. Subfamilies of chemokines and corresponding chemokine receptor are defined by the position of the first two cysteine residues on chemokines: the CXC chemokines, which bind any of the five lymphocyte-specific receptors, CXCR1-CXCR5; the CC chemokines, with 24 members that bind to CCR1-CCR11, found on most types of leukocytes; one C chemokine, termed lymphotactin, which binds to CXCR1; and one C3XC chemokine, fractalkine, which binds CXCR1. MSCs have been shown in some studies to express some chemokines and their receptors at relatively low levels (Dazzi, et al. (2006) surpa), but there is no information related to the possible role of activated T cells in the induction of chemokine expression by MSCs.

SUMMARY OF THE INVENTION

The present invention is a composition comprising (a) isolated mesenchymal stem cells; (b) isolated interferon gamma; and (c) isolated interleukin-1 alpha, interleukin-1 beta or tumor necrosis factor alpha, in admixture with a pharmaceutically acceptable carrier. A kit for attenuating an immune response is also provided.

The present invention also embraces a method for attenuating an immune response by administering an effective amount of the composition the invention to a subject in need of treatment.

A method for enhancing a local immune response is also provided. This method involves administering to a subject in need of treatment an effective amount of iNOS-deficient or IDO-deficient mesenchymal stem cells thereby enhancing a local immune response. In certain embodiments, the local immune response is to a vaccine or tumor.

The present invention further embraces a method for enhancing interferon gamma treatment of cancer by administering to a subject receiving interferon gamma treatment an effective amount of a nitric oxide synthase inhibitor. In particular embodiments the inhibitor is an iNOS inhibitor.

DETAILED DESCRIPTION OF THE INVENTION

Figure 1:
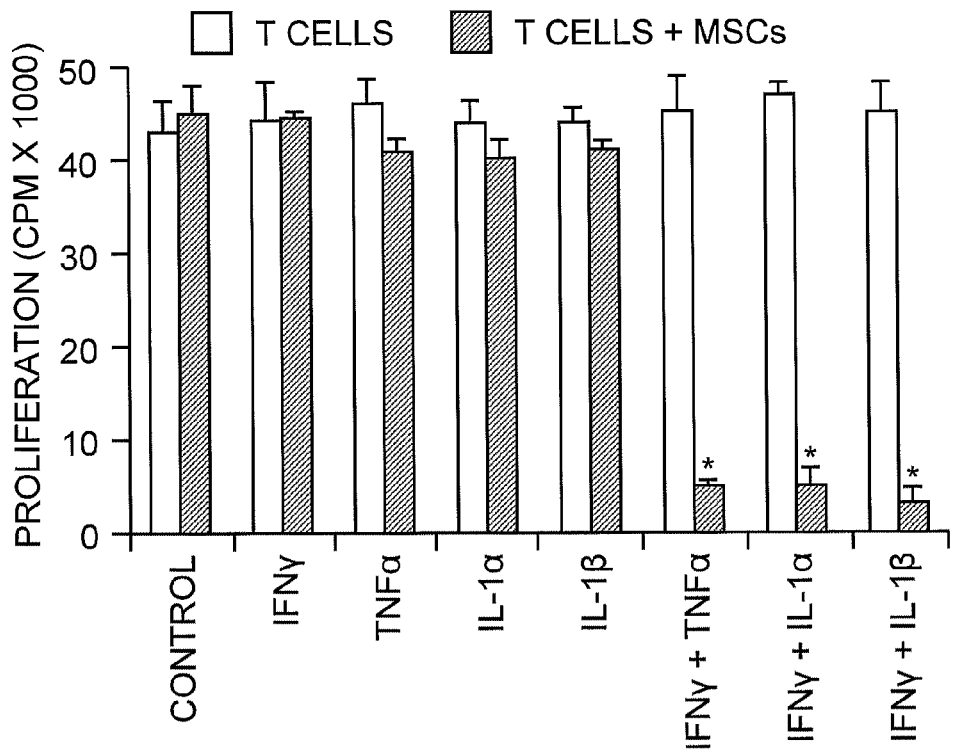
FIG. 1 is a graph showing that immunosuppression by MSCs is induced by proinflammatory cytokines. Cloned MSCs were supplemented with the indicated combinations of recombinant cytokines (20 ng/ml each) for 8 hours, then co-cultured with $CD4^+$ T cell blasts at a 1:20 ratio (MSC:T cells), and proliferation assessed after an additional 8 hours. Values represent means±SD of five wells from a representative of three experiments with different clones. * p<0.001.

IFNγ has been previously reported to be important in immunosuppression by human MSCs (Krampera, et al. (2006) Stem Cells 24:386-398; Plumas, et al. (2005) Leukemia 19:1597-1604). These studies concluded that IFNγ-induced indoleamine 2,3-dioxygenase (IDO) mediates immunosuppression. However, the results presented herein demonstrate that IFNγ alone is insufficient. It has now been demonstrated that the expression of iNOS and chemokines is dramatically increased by the addition of IFNγ when provided in combination with a T-cell cytokines (e.g., TNFα, IL-1α or IL-1β, which were found to function interchangeably). Additionally, it was demonstrated that indeed these chemokines have strong chemotactic activity and promote lymphocyte migration into the vicinity of MSCs, which produce large amounts of NO. In vivo, MSCs blocked delayed-type hypersensitivity (DTH) and prevented the development of graft-versus-host disease through a mechanism requiring IFNγ and iNOS. It was also observed that MSC-like cells derived from tumors also inhibited immune responses and promoted tumor growth. Thus, this analysis revealed a fundamental mechanism through which NO, IDO and chemokines mediate the immunosuppressive activity of MSCs. Accordingly, the present invention relates to the modulation of the immune system using MSCs combined with inflammatory cytokines. MSCs used in accordance with the present invention find application in the treatment of various degenerative diseases and immune disorders.

The analysis presented herein demonstrates that immunosuppression by MSCs is exerted through the coordinated action of cytokine-induced chemokines and NO, In vitro, chemical blockade of iNOS or IDO reverts immunosuppression. In addition, injection of $iNOS^{-/-}$ MSCs actually enhances the DTH response, confirming the role of iNOS in vivo, and indicating that MSCs recruit lymphocytes. While not wishing to be bound by theory, the results herein indicate the following. Chemokines produced by MSCs attract lymphocyte to the site of antigenic challenge, where their activity is inhibited by MSC-produced NO. Without NO, lymphocytes remain fully-functional, increasing the immune reactivity. Based on this premise, it is contemplated that in the presence of an active immune reaction, administered MSCs localize to the inflammatory site, immediately acquire immunosuppressive function, and thus become effective in attenuating the ongoing immune response. On the other hand, in the absence of tissue damage and active inflammation, administered MSCs would neither localize specifically nor become immunosuppressive.

Based upon the concerted activity of the combination of stem cells and cytokines disclosed herein, the present invention embraces a composition composed of mesenchymal stem cells, IFNγ, and one or more of IL-1α, IL-1β, or TNFα for use in modulating an immune response.

Mesenchymal stem cells (MSC) are multipotent progenitors for a variety of cell types of mesenchymal cell lineage, including bone, cartilage, fat, tendon, nerve tissue, fibroblasts and muscle cells. Mesenchymal stem cells can be isolated and purified from tissue such as bone marrow, blood (including peripheral blood), periosteum, and dermis, and other tissues which have mesodermal origins. In this regard, it has been found that although these progenitor mesenchymal stem cells are normally present in bone marrow, for example, in very minute amounts and that these amounts greatly decrease with age (i.e., from about 1/10,000 cells in a relatively young patient to as few as 1/2,000,000 in an elderly patient), human mesenchymal stem cells can be isolated from various tissues and purified when cultured in a specific medium by their selective attachment, termed "adherence," to substrates.

The isolated mesenchymal stem cells of this invention can be a homogeneous composition or can be a mixed cell population enriched in MSCs. In this regard, an isolated population of MSCS is composed of at least about 75% MSCs, or at least about 83%, 84%, 88%, 89%, 90%, 91%, 93%, 95%, 96%, 97%, or 98% MSCS.

The human mesenchymal stem cells can be derived, for example, from bone marrow obtained from a number of different sources, including plugs of femoral head cancellous bone pieces, obtained from patients with degenerative joint disease during hip or knee replacement surgery, and from aspirated marrow obtained from normal donors and oncology patients who have marrow harvested for future bone marrow transplantation. Although the harvested marrow is generally prepared for cell culture separation by a number of different mechanical isolation processes depending upon the source of the harvested marrow (i.e., the presence of bone chips, peripheral blood, etc.), the critical step involved in the isolation processes is the use of a specially prepared medium that contains agents that allow for not only mesenchymal stem cell growth without differentiation, but also for the direct adherence of only the mesenchymal stem cells to the plastic or glass surface area of the culture dish. By producing a medium that allows for the selective attachment of the desired mesenchymal stem cells, which are present in the marrow samples in very minute amounts, it is possible to separate the mesenchymal stem cells from the other cells (i.e., red and white blood cells, other differentiated mesenchymal cells, etc.) present in the bone marrow.

While the invention is not limited to the use of mesenchymal stem cells obtained by any particular method, MSC can be isolated from bone marrow, purified and culturally-expanded as follows. Plugs or aspirates of bone marrow are processed to remove bone pieces and fat. The marrow cells (consisting predominantly of red and white blood cells, and a very minute amount of mesenchymal stem cells) are passed through syringes to dissociate the tissue into single cells. The cells are cultured in complete medium (e.g., MEM medium with 10% fetal bovine serum) and humidified atmosphere. The media is not changed for at least one day to allow the cells to attach to the culture dish. Thereafter the media is replaced every 3-4 days. When the cells have grown to confluence, the cells are detached from the culture dish, preferably with trypsin. Cells can be subcultured in serum-free media after removal or inactivation of the trypsin. Additional methods for isolating and culturing mesenchymal stem cells are provided in US Patent Application Nos. 20070160583 and 20070128722.

Mesenchymal stem cells are typically identified based upon the expression or lack of expression of particular markers. For example, MSCs are $CD34^-$, $CD11b^-$, $CD11c^-$, $CD45^-$, MHC class $II^-$, $CD44^+$, $Sca-1^+$, and MHC class $I^{low}$.

In addition, MSCs can be identified by their ability to differentiate into various mesenchymal cell types. In vitro experiments have demonstrated that culture conditions, additives, growth factors and cytokines can precisely induce MSC to develop into a selected mesenchymal tissue. For example, dexamethasone in combination with isobutilmethylxanthine or insulin or a mixture of isobutilmethylxanthine, insulin and indomethacin has been shown to push the MSCs toward differentiating into adipocytes. Similarly, MSCs can differentiate into skeletal muscle cells when stimulated with 5-azacytidine. β-FGF has been shown to cause mesenchymal stem cells to differentiate into cardiac muscle cells.

The mesenchymal stem cells used in accordance with the invention are, in order of preference, autologous, allogeneic or xenogeneic, and the choice can largely depend on the urgency of the need for treatment.

The cytokines of the present invention are well-known in the art and can be obtained by conventional purification methods, by recombinant technologies or from commercial sources. For example, the amino acid sequence of interferon-gamma (IFNγ) is provided under GENBANK Accession Nos. NP_000610 (human) and NP_032363 (mouse). Commercial sources of IFNγ protein include, e.g., INTERMUNE (Brisbane, Calif.) and PeproTech, Inc. (Rocky Hill, N.J.). Likewise, tumor necrosis factor-alpha (TNFα, cachexin or cachectin) is provided under GENBANK Accession Nos. NP_000585 (human) and NP_038721 (mouse) and commercially available from sources such as ProSpec Bio (Rehovot, Israel) and PeproTech, Inc. Similarly, human interleukin 1-alpha (IL1α) and interleukin 1-beta (IL1β) are known under Accession Nos. P01583 and P01584, respectively, and are available from commercial sources such as ProSpec Bio and PeproTech, Inc. When used in accordance with this invention, the cytokines are "isolated," i.e., either homogenous (100%) or near homogenous (90 to 99%). In particular embodiments, the cytokine are recombinant proteins.

The present invention provides the above-referenced MSCs and cytokines in the form of a composition, e.g., a pharmaceutical composition suitable for administration to a subject in need of treatment with the same. The compositions of the invention can be administered by any conventional method including parenteral (e.g., subcutaneous or intramuscular) or intravenous injection, intravenous infusion, or topical application. The treatment can be composed of a single dose or a plurality of doses over a period of time. The pharmaceutical composition typically contains at least one acceptable carrier. The carrier must be "acceptable" in the sense of being compatible with the MSCs and cytokines and not deleterious to the recipients thereof. Typically, the carrier can be a suitable isotonic solution such as phosphate-buffered saline, culture media, such as DMEM, physiological saline, 5% aqueous dextrose, and/or mixtures thereof, and other suitable liquids known to those skilled in the art.

For use therapeutically, the pharmaceutical composition of the invention can be provided as a kit. A kit of the invention contains a pharmaceutically acceptable carrier; an isolated population of mesenchymal stem cells; isolated IFNγ; and isolated IL1α, IL1β or TNFα and can also contain instructions for using the kit in a method for attenuating an immune response. The cell and cytokine components of the kit can be administered individually, or combined in vitro and subsequently administered as a mixture. The kit also optionally may include a means of administering the composition, for example by injection.

The present invention also embraces a method for attenuating an immune response by administering an effective amount of MSCs and cytokines (i.e., IFNγ and IL1α, IL1β or TNFα) to a subject in need of treatment. In one embodiment, the MSCs are provided as a pharmaceutical composition, wherein the MSCs are formulated with a cytokine cocktail prior to administration. In another embodiment, the MSCs and cytokines are administered as individual components. A subject in need of treatment can be a mammal (e.g., a human, monkey, dog, cat, horse, etc.) with a particular disease or disorder associated with an adverse immune response. In particular embodiments, the subject is human. For the purposes of this invention an "effective amount" refers to that amount of MSCs and cytokines that is sufficient to attenuate an immune response (i.e., suppression of T cell responses) in the subject thereby reducing at least one sign or symptom of the disease or disorder. Effectiveness can also be determined by monitoring iNOS, IDO, and/or chemokine expression. Subjects benefiting from attenuation of an adverse immune response include subjects having or suspected of having an autoimmune disorder (e.g., rheumatoid arthritis, diabetes mellitus type 1, systemic lupus erythematosus, Scleroderma, or psoriasis), allergy (e.g., hay fever), or sepsis. In addition, because inflammation orchestrates the microenvironment around tumors, contributing to proliferation, survival and migration, certain cancer patients may also benefit from the present composition.

In organ transplant and bone marrow transplant, T cells of donor origin can recognize the recipient's MHC and lead to the development of GvHD. This often fatal disease is frequently unresponsive to various immunosuppressive therapies (Lu, et al. (1996) *Crit. Rev. Oncol./Hematol.* 22:61-78; Shlomchik (2007) *Nat. Rev. Immunol.* 7:340-352), but new approaches targeting immune modulatory molecules show great promise in treating GvHD (Jacobsohn (2002) *Exp. Opin. Investigat. Drugs* 11:1271-1280; Tamada, et al. (2000) *Nat. Med.* 6:283-289; Xu, et al. (2007) *Blood* 109:4097-4104). Most recently, MSCs have been shown to be highly effective in the treatment of GvHD in pre-clinical and clinical trials (Aggarwal & Pittenger (2005) supra). The analysis presented herein further demonstrates that MSC activity is mediated via the production of NO or IDO after stimulation with pro-inflammatory cytokines. Accordingly, the composition of this invention finds use in organ transplantation or treatment of graft-versus-host disease.

In vivo determination of suitable doses can be accomplished using art-accepted animal models such as the DTH and GvHD models described herein. However, as the present involves treatment under the care of a physician or veterinarian, adjustments can be made to the amount and timing of treatment during the course of treatment, based on the evaluation of the effectiveness of the treatment, which can vary from subject to subject. In addition, treatment can be provided at particular stages of immune responses in patients as described by the physician or veterinarian.

Having demonstrated that, in the absence of NO production, MSC-mediated chemotaxis can enhance an immune response (e.g., inflammation in response to an antigen), the present invention also embraces a method for enhancing a local immune response by administering to a subject in need of treatment an effective amount of inducible nitric oxide synthase (iNOS)-deficient and/or indoleamine 2,3-dioxygenase (IDO)-deficient mesenchymal stem cells. MSCs that are deficient in iNOS and/or IDO activity are defined as MSCs that exhibit less than 30%, 40%, 50%, 60%, 70% or 80% IDO and/or iNOS activity as compared to wild-type MSCs. iNOS-deficient or IDO-deficient MSCs can be generated by conventional mutagenesis methods or site-specific mutagenesis to delete all or a part of the iNOS or IDO open reading frame thereby decreasing the expression and activity of iNOS and/or IDO. In an alternative embodiment, MSCs can be made iNOS- and/or IDO-deficient by treatment with iNOS- and/or IDO-selective inhibitors. Suitable iNOS inhibitors include, e.g., 1400 W, GW274150 (Dugo, et al. (2004) *Br. J. Pharmacol.* 141:979-987), aminoguanidine, L-$N^6$-(1-iminoethyl) lysine, and S-alkylated isothiourea derivatives (Southan & Szabo (1996) *Biochem. Pharmacol.* 51:383-394). Suitable IDO inhibitors include, e.g., 1-methyl-tryptophan (1-MT) and Exiguamine A. See also, WO 2006/005185 Subjects benefiting from treatment with the iNOS- and/or IDO-deficient MSCs include subjects receiving a vaccine, wherein enhancement of a local immune response can increase response to the vaccine antigen (as compared to a vaccine administered in the absence of iNOS- and/or IDO-deficient MSCs), or a subject with a tumor, wherein iNOS- and/or IDO-deficient MSCs provoke effective immune responses to tumors.

Interferon treatment has been indicated for use in the treatment of a several cancers including, e.g., ovarian cancer (U.S. Pat. No. 5,268,169) and primary cancers of pleura (U.S. Pat. No. 5,108,743). The data presented herein indicate that the efficacy of IFN treatment or similar immune cancer therapies can be increased by suppressing NO production or IDO activity in the tumor microenvironment. Accordingly, the present invention also embraces a method for enhancing the efficacy of an immune therapy of cancer by administering to a subject receiving an immune therapy treatment an effective amount of a nitric oxide synthase (NOS) and/or IDO inhibitor. In particular embodiments, the inhibitors are IDO and iNOS-selective inhibitors, e.g., as disclosed herein. An effective amount of such an inhibitor is an amount which provides at least a 50%, 60%, 70%, 80%, 90%, 95%, or 97% decrease in the amount of NO production and/or IDO activity upon administration of the immune therapy as compared to a subject not receiving the inhibitors. In a particular embodiment, the method embraces enhancing the therapeutic effectiveness of an interferon treatment (e.g., IFNγ) using an IDO and/or iNOS-selective inhibitor.

The following non-limiting examples are provided to further illustrate the present invention.

Example 1

Materials and Methods

Mice.
Male C57BL/6, C3H/HeJCr and F1 (C57BL/6×C3H) mice, 6-8 weeks old, were from the National Cancer Institute (Frederick, Md.). IFNγ-R1$^{-/-}$ mice (Ifngr1$^{tm1Agt}$) and iNOS$^{-/-}$ mice (Nos2$^{tm1Lau}$) were from Jackson Laboratory (Bar Harbor, Me.). Mice were maintained in the Robert Wood Johnson Medical School Vivarium. Animals were matched for age and gender in each experiment, all approved by the Institutional Animal Care and Use Committee.

Reagents.
Recombinant mouse IFNγ, TNFα, IL-1α, and IL-1β, monoclonal antibodies against mouse TNFα, IL-1α, IL-1β and CCR5, FITC-conjugated anti-mouse CD11b, and PE-conjugated anti-mouse F4/80 were from eBiosciences (La Jolla, Calif.). Recombinant mouse M-CSF and antibodies against IL-10 and TGF-β were from R&D Systems (Minneapolis, Minn.). Anti-IFNγ was from Harlan (Indianapolis, Ind.). Anti-CXCR3 was from Invitrogen (Carlsbad, Calif.). Indomethacin, 1-methyl-DL-tryptophan (1-MT), and $N^G$-monomethyl-L-arginine (L-NMMA) were from Sigma-Aldrich (St. Louis, Mo.).

Cells.
MSCs were generated from bone marrow of tibia and femur of 6-10 week old mice. Cells were cultured in α-MEM medium supplemented with 10% FBS, 2 mM glutamine, 100 U/ml penicillin, and 100 µg/ml streptomycin (all from Invitrogen). Non-adherent cells were removed after 24 hours, and adherent cells were maintained with medium replenishment every three days. To obtain MSC clones, cells at confluence were harvested and seeded into 96-well plates by limited dilution. Individual clones were then picked and expanded. Cells were used at $5^{th}$ to $20^{th}$ passage.

T cell blasts were generated from CD4$^+$ T cells purified by negative selection with CD4$^+$ T cell subset isolation kits (R&D Systems). Cells (1×10$^6$ cells/ml) were activated by plastic-bound anti-CD3 and soluble anti-CD28 for 48 hours, then cultured with IL-2 (200 U/ml) alone for 48 hours. All T cell cultures were maintained in RPMI-1640 medium supplemented with 10% heat-inactivated FBS, 2 mM glutamine, 100 U/ml penicillin, 100 µg/ml streptomycin, and 50 mM β-ME (complete medium).

Activated splenocyte supernatant was harvested from 48 hour-cultures of splenocytes (2×10$^6$/ml) activated by plastic-bound anti-CD3, then filtered with a 0.1 µm filter and frozen.

Detection of Cytokines, Chemokines, and NO.
Culture supernatants were assayed for 20 different cytokines and chemokines with a multiplex bead array kit (Invitrogen, Carlsbad, Calif.) using Luminex Technology (Bio-Plex System, Bio-Rad, Hercules, Calif.). IFNγ was assayed by ELISA (BD Biosciences, San Jose, Calif.). NO was detected using a modified Griess reagent (Sigma-Aldrich). Briefly, all NO$_3$ was converted into NO$_2$ by nitrate reductase, and total NO$_2$ detected by the Griess reaction (Miranda, et al. (2001) *Nitric Oxide* 5:62-71).

Real-Time PCR.
RNA was isolated from cell pellets using an RNEASY Mini Kit. First-strand cDNA synthesis was performed using SENSISCRIPT RT Kit with random hexamer primers (all kits from Qiagen, Valencia, Calif.). mRNA of the genes of interest were quantified by real-time PCR (MX-4000 from Stratagene, La Jolla, Calif.) using SYBR Green Master Mix (Applied Biosystems, Foster City, Calif.). Total amount of mRNA was normalized to endogenous β-actin mRNA. Primers sequences for iNOS were: forward, 5'-CAG CTG GGC TGT ACA AAC CTT-3' (SEQ ID NO:1); reverse, 5'-CAT TGG AAG TGA AGC GTT TCG-3' (SEQ ID NO:2). Other primers were from the RT² PROFILER™ PCR Array Mouse Chemokines & Receptors kit (Superarray, Frederick, Md.).

Chemotaxis Assay.

Chemotaxis was tested with the NeuroProbe CHEMOTX Chemotaxis System (NeuroProbe, Gaithersburg, Md.), as described (Shi, et al. (1993) *J. Immunol. Meth.* 164:149-154). The lower chambers of the 96-well plate were filled with supernatant from MSCs stimulated with IFNγ plus TNFα (20 ng/ml each or $Sup_{CD3-act}$ (1:2 dilution). A polyvinylpyrrolidine-free polycarbonate membrane with 5 μm pores was then overlaid. T cell blasts ($1.25 \times 10^5$) were added to the top chambers. After a 3-hour incubation, cells that had migrated through pores and into bottom wells were quantified using MTT assay (Shi, et al. (1993) supra). A chemotaxis index was calculated as the ratio of the number of T cell blasts migrated in response to MSCs compared to the number migrating to medium alone.

The immunosuppression resulting from T cell migration toward inflammatory cytokine-activated MSCs was examined in a similar set-up. MSCs ($2 \times 10^4$) were added to the lower chamber with or without stimulation with IFNγ and TNFα (20 ng/ml each) for 24 hours. Activated T cell blasts were then added to the upper chamber, as above. IL-2 was added to both chambers. After 3 hours, both chambers were pulsed with $^3$H-thymidine, and cell proliferation assessed 6 hours later.

GvHD Induction and Modulation by MSCs.

C57BL/6×C3H F1 mice at 8-weeks old were lethally irradiated (13 Gy) and after 24 hours were infused by tail vein injection with nucleated bone marrow cells ($5 \times 10^6$) and splenocytes ($5 \times 10^6$) isolated from C57BL/6 parent mice. On days 3 and 7 following bone marrow transplantation, the recipients were administrated with $0.5 \times 10^6$ MSCs derived from C57BL/6 wild-type, IFNγR1$^{-/-}$, or iNOS$^{-/-}$ mice via the tail vein. Some wild-type MSC groups were also injected i.p. with the iNOS inhibitor, $N^G$-monomethyl L-arginine (L-NMMA, 500 μg/mouse), anti-IFNγ (400 μg/mouse), or a cocktail of three antibodies against TNFα, IL-1α, and IL-1β (200 μg each/mouse) daily for 7 days starting immediately after the first MSC administration. As negative controls, the F1 mice were injected with F1 bone marrow cells. Mice were observed daily for GvHD signs (wasting, ruffled hair, and hunched back) and euthanized upon becoming moribund, thus marking survival time. On day 14, various tissues were collected and 5-μm paraffin sections prepared and stained with hematoxylin/eosin (H&E).

Induction of DTH Response and Histology Analysis.

C57BL/6 mice (6-8 weeks old) were immunized by tail base injection of ovalbumin (OVA, 10 μg in 50 μl saline) emulsified with 50 μl complete Freund's adjuvant. DTH was tested after 5 days, by challenging with 200 μg aggregated OVA in 30 μl saline injected into the right hind footpad. The left footpad was injected with 30 μl of saline as a negative control. After 24 hours, antigen-induced footpad thickness increment was measured using a caliper and calculated as: $(R_{imm}-L_{imm})-(R_{unimm}-L_{unimm})$, where R and L are thickness of right and left footpads.

Statistical Analysis.

Significance was assessed by unpaired two-tailed Student's t-test or analysis of variance (ANOVA).

Example 2

Immunosuppressive Function of MSCs is Induced by Proinflammatory Cytokines

Several studies have shown that MSCs are immunosuppressive (Inoue, et al. (2006) supra; Le Blanc, et al. (2004) *Lancet* 363:1439-1441; Rasmusson (2006) *Exp. Cell Res.* 305:33-41; Uccelli, et al. (2006) *Eur. J. Immunol.* 36(10): 2566-73; Xu, et al. (2007) *Cell Res.* 17:240-248). To identify the underlying mechanisms, clones of mouse MSCs were employed. The stem cell characteristics of these clones were defined by their ability to differentiate into adipocytes or osteoblasts and by their expression of surface markers: CD34$^-$CD11b$^-$CD11c$^-$CD45$^-$MHC class II$^-$CD44$^+$Sca-1$^+$ MHC class I$^{low}$. All results presented herein were replicated using at least three different MSC clones.

Since most reported studies of immunosuppression by MSCs are based on their effects on T cell proliferation and cytokine production, the effect of MSCs was first examined on the IL-2-driven proliferation of T cell blasts. Fresh CD4$^+$ T cell blasts were generated from splenocytes by activation with anti-CD3 followed by expansion with IL-2 for several days (Devadas, et al. (2006) *Immunity* 25:237-247; Radvanyi, et al. (1996) *Cell Immunol.* 170:260-273). T cell blasts were added at a 1:20 ratio (MSC:T cells) along with IL-2 (200 U/ml). Cell proliferation was assessed by $^3$H-Tdr incorporation after 8 hours. Surprisingly, it was found that the IL-2 driven proliferation of these T cell blasts was unaffected by the addition of MSCs. MSCs also had no effect on the proliferation of T hybridoma A1.1 cells. These T cells blasts and T hybridoma cells, however, produce no cytokines unless reactivated through the TCR (Fotedar, et al. (1985) *J. Immunol.* 135(5):3028-33). Thus, in the absence of T cell cytokines, MSCs were unable to suppress T cell proliferation.

Most previous studies that have concluded that MSCs are immunosuppressive have examined the outcome of co-cultures in which T cells are mixed with MSCs during their activation. In this case, the MSCs are exposed to cytokines produced by the activated T cells, and these cytokines may have a role in inducing the immunosuppressive capacity of MSCs, which in turn would suppress T cell proliferation. To examine the possibility that cytokines induce the immunosuppressive capacity of MSCs, these culture conditions were reproduced by combining MSCs and fresh splenocytes at graded ratios in the presence of anti-CD3. The results of this analysis indicated that T cell proliferation was completely blocked when MSCs were added at a ratio as low as 1:60 (MSC to splenocyte). Importantly, to exert their immunosuppressive effect, MSCs do not have to be syngeneic. A similar effect was found on purified CD4$^+$ or CD8$^+$ T cells activated by plastic-bound anti-CD3 antibody and anti-CD28 using MSCs from between the 5$^{th}$ and 20$^{th}$ passage. Thus, under conditions in which MSCs and T cells are in co-culture during T cell activation, the resultant T cell response was strongly suppressed by MSCs, indicating that T cell-produced cytokines may have a role. The immunosuppressive capacity of MSC clones generated from different mouse strains was also examined. It was observed that those clones that exhibited better differentiation potential had a greater capacity for immunosuppression.

To determine whether cytokines secreted by activated T cells are responsible for the induction of immunosuppression by MSCs, mixed co-cultures of MSCs with T cell blasts (as described above) were supplemented with supernatant from a culture of anti-CD3-activated splenocytes. The resultant T cell proliferation was greatly inhibited. It was also observed that the proliferation of A1.1 cells in co-culture with MSCs was inhibited by supplementation with the activated splenocyte supernatant. These experiments indicate that some product(s) of activated T cells is required to induce immunosuppression by MSCs. To identify the culpable cytokine(s), the activated splenocyte supernatant was treated with neutralizing antibodies against various cytokines before addition to the co-cultures. This analysis indicated that neutralization of IFNγ completely reversed the inhibition of proliferation of T cell blasts co-cultured with MSCs supplemented with the anti-CD3-activated splenocyte supernatant. These results implicate IFNγ as a key cytokine in this process, and reveal that under certain conditions this major proinflammatory cytokine can instead mediate immunosuppression.

The effect of IFNγ was then tested directly by adding isolated recombinant IFNγ (20 ng/ml) instead of activated splenocyte supernatant to the mixed co-cultures of MSC+T cell blasts or MSC+A1.1 cells. Surprisingly, IFNγ alone did not induce immunosuppression. Several other proinflammatory cytokines were then added (20 ng/ml each) and it was found that concomitant addition of either TNFα, IL-1α, or IL-1β along with IFNγ was required to achieve suppression of T cell proliferation in co-cultures with MSCs (1:20 ration MSC:T cells) (FIG. 1). Therefore, induction of the immunosuppressive function of MSCs by anti-CD3-activated splenocyte supernatant may be due to IFNγ acting in concert with either TNFα, IL-1α, or IL-1β on the MSCs. Thus, while IFNγ is absolutely required, this cytokine alone is not sufficient; proper immunosuppression signaling in MSCs requires the concerted action of IFNγ and any of the other three cytokines. To further dissect the role of these cytokine combinations, neutralizing antibodies against TNFα, IL-1α, or IL-1β, individually or together, were added to the activated splenocyte supernatant before addition to mixed co-cultures of MSCs and T cell blasts. While individual antibodies had no effect, simultaneous blockade of all three cytokines completely reversed the inhibition of T cell proliferation. Other cytokines, such as GM-CSF (Granulocyte-macrophage colony-stimulating factor) and IL-6 (Interleukin-6), had no effect. It is important to point out that although IL-1α and IL-1β are not produced to a great extent by T cells, they can be produced by antigen presenting cells within the splenocyte population in the presence of T cell cytokines. The data herein indicate that the combination of IFNγ with any of the other three proinflammatory cytokines, TNFα, IL-1α, or IL-1β is responsible for inducing the ability of MSCs to inhibit T cell proliferation, and that TNFα, IL-1α, and IL-1β are interchangeable in acting together with IFNγ.

MSCs not only efficiently blocked activation-induced splenic T cell proliferation, but also inhibited the production of cytokines such as IFNγ, IL-4 and TNFα. It is ironic that MSCs strongly inhibit T cell production of IFNγ, which at the same time is essential to induce immunosuppression by MSCs. It was reasoned that MSCs must encounter some level of IFNγ arising from initial T cell activation. Indeed, it was found that MSCs do not affect the initial T cell response when present during their anti-CD3-induced activation, as demonstrated by normal increases in CD69 expression. As further evidence that IFNγ released from splenocytes after initial activation was key to inducing immunosuppression by MSCs, it was observed that MSCs derived from mice deficient in IFNγ receptor 1 (IFNγR1−/−) were incapable of immunosuppression. Several clones of these IFNγR1−/− MSCs were derived (all capable of differentiation into adipocytes and osteoblast-like cells), and none of the five clones tested were able to suppress anti-CD3-induced splenocyte proliferation, supporting the understanding that IFNγ is essential in the induction of the immunosuppressive function of MSCs. These results indicate that the initial production of IFNγ and other cytokines by cells in close proximity to MSCs are critical to induce the immunosuppressive capacity. Indeed, anti-IFNγ (20 μg/ml) also completely blocked the suppressive effect of MSCs in this setting. In addition, although antibodies against TNFα, IL-1α, or IL-1β (20 μg/ml each) were ineffective individually, immunosuppression was prevented when all three antibodies were added together, similar to their effect when added to activated splenocyte supernatant. Therefore, the concomitant action of locally-produced IFNγ along with TNFα, IL-1α, or IL-1β is sufficient to induce MSCs to become immunosuppressive.

Example 3

Immunosuppression by MSCs Requires Nitric Oxide

To identify the mechanism through which immunosuppression by cytokine-exposed MSCs is effected, the response of anti-CD3-activated splenocytes co-cultured with MSCs (1:20, MSC:splenocytes) in a TRANSWELL system was examined in various configurations. When separated by a permeable membrane (0.4 μm pore membrane) in the two chambers of the well, MSCs had almost no effect on T cell proliferation, indicating that a cell membrane-associated protein or other local acting factor(s) was critical for the suppression of T cell proliferation by cytokine-primed MSCs. While a recent report (Sato, et al. (2007) supra) showed that PGE-2, but not IDO, is required, it was found that PGE-2 was not involved. In fact, no effect was found on immunosuppression by MSCs by indomethacin (10 μM, a PGE-2 blocker), anti-IL-10 (20 μg/ml), anti-TGFβ (20 μg/ml) or 1-methyl-DL-tryptophan (1-MT, 1 mM, an IDO inhibitor), thereby ruling out these factors.

Nitric oxide (NO) at high concentrations is known to inhibit T cell responses (Denham & Rowland (1992) *Clin. Exp. Immunol.* 0.87(1):157-62; Isobe & Nakashima (1993) *J. Cell Biochem.* 53(3):198-205). It diffuses quickly from its source (Lancaster (1997) *Nitric Oxide* 1:18-30; Vaughn, et al. (1998) *Am. J. Physiol.* 274:H2163-2176), but the concentration of the active form drops off within about 100 μm. Therefore, NO can act only in close proximity to the cells producing it, which is consistent with the predicted characteristics of the factor that mediates immunosuppression by MSCs. To determine whether NO had such a role, its production was shut down using a selective inhibitor of iNOS activity, NG-monomethyl-L-arginin (L-NMMA). When added to mixed co-cultures of MSCs and splenocytes in the presence of anti-CD3, L-NMMA completely restored normal splenocyte proliferation. Other iNOS inhibitors such as 1400 W and L-NAME showed the same effect. Furthermore, MSCs derived from mice deficient in iNOS (iNOS$^{-/-}$) had almost no effect on splenocyte proliferation. In addition, of five clones of iNOS$^{-/-}$ MSCs derived (all capable of differentiation into adipocytes and osteoblast-like cells), none were immunosuppressive. These results indicate that the activity of NO produced by MSCs in response to cytokine-induction mediates their suppression of T cell responses.

The analysis herein indicates that immunosuppression by MSCs is induced by IFNγ and proinflammatory cytokines and is mediated through NO. Accordingly, it was contemplated that MSCs could upregulate their expression of iNOS and produce NO after exposure to these cytokines. To examine this, MSCs were treated with activated splenocyte supernatant and the level of iNOS mRNA assayed by real-time PCR and compared to β-actin. The results of this analysis indicated that iNOS was significantly upregulated in MSCs by 4 hours after stimulation, with high-level expression sustained for at least 48 hours. At 12 hours post-stimulation, the level of iNOS mRNA was more than 7 times greater than β-actin message, indicative of extremely high expression. A similar effect was observed when IFNγ and TNFα (20 ng/ml each) were added together, while either alone was ineffective. In addition, IL-1α and IL-1β were again interchangeable with TNFα in this regard. When antibodies were added to neutralize cytokine activities in anti-CD3-activated splenocyte supernatant, it was observed that anti-IFNγ alone, or the 3-antibody combination against TNFα, IL-1α and IL-1β, prevented iNOS upregulation by MSCs. When antibodies against TNFα, IL-1α or IL-1β were used singly or doubly, there was no effect. Therefore, the same cytokines that induce immunosuppression are also potent inducers of iNOS expression by MSCs.

To determine whether iNOS expression in cytokine-treated MSCs indeed leads to NO production, two stable breakdown products of NO, nitrate ($NO_3$) and nitrite ($NO_2$), were measured in conditioned medium from MSCs treated with anti-CD3-activated splenocyte supernatant. The amount of $NO_2$ produced by MSCs after treatment was at least 10 times greater than that from similarly treated $CD11b^+F4/80^+$ macrophages, which are known to be abundant producers of NO. These results are consistent with the high levels of iNOS mRNA expression described herein. Thus, upregulation of iNOS expression by MSCs in response to proinflammatory cytokines leads to production of NO, which can act on T cells in close proximity.

It has been reported that in the absence of T cell activation or exogenous inflammatory cytokines, MSCs can prolong the survival of lymphocytes (Xu, et al. (2007) *Biochem. Biophys. Res. Comm.* 361:745-750). In the present study, with T cell activation or when exogenous inflammatory cytokines are added, the T cells first enter cell cycle arrest and then die within 24 hours. It was also observed that this apoptosis was dependent on NO, since T cell apoptosis was not observed when iNOS inhibitors were used. Apoptosis was also absent when $iNOS^{-/-}$ or $IFN\gamma R1^{-/-}$ MSCs were used. Therefore, NO-induced cell cycle arrest and apoptosis of T cells are part of the mechanism of immunosuppression mediated by inflammatory cytokine-activated MSCs. Differences between species in inflammatory cytokine-induced expression of iNOS has been noted in macrophages (Schneemann & Schoedon. 2002) *Nat. Immunol.* 3(2):102). NO was found to be induced by inflammatory cytokines in macrophages of mouse, rat, and bovine origin, but not caprine, lapin, porcine, and human macrophages (Schneemann & Schoedon (2002) supra; Jungi, et al. (1996) *Vet. Immunol. Immunopathol.* 54:323-330). Thus, the roles of IDO and NO in the inhibition of T cell proliferation by MSCs from mouse and human were analyzed in a side-by-side comparison. It was found that inhibition of NO by L-NMMA completely reversed immunosuppression by mouse MSCs, whereas the inhibition of peripheral blood mononuclear cell proliferation by human MSCs was reversed by 1-MT, indicating that MSCs from humans utilize IDO as the major effector of immunosuppression, in comparison to mouse MSCs which utilize NO.

Example 4

Chemoattractive Property of MSCs is Induced by Proinflammatory Cytokines

In several studies, effective immunosuppression by MSCs in vivo has been achieved with as few as one to five MSCs per million somatic cells and often endures for months, with complete cure of immune disorders in some instances. Considering that MSCs are immobile after settling in tissues, and that immunosuppression is mediated by NO, which acts only very locally near its source, this immunosuppressive effect is astonishing. It was contemplated that cytokine-induced MSCs might have a mechanism to attract immune cells to their vicinity, where the locally high concentrations of NO could act effectively on the target T cells. To explore this, co-cultures of MSCs and splenocytes were monitored over time under the microscope. Upon anti-CD3-stimulation, the splenocytes were observed to actively migrate toward the spindle-shaped MSCs. In contrast, no migration occurred in the absence of anti-CD3 stimulation. Since splenocytes have limited viability, the lack of locomotion toward MSCs in the absence of stimulation might be due to the poor health of these cells in vitro. To exclude this, activated-splenocyte-supernatant-primed MSCs were examined for their ability to attract A1.1 T hybridoma cells, which survive well even in the absence of IL-2. Under these conditions, time-lapse microvideography revealed brisk migration of T cells toward MSCs within 1.5 hours of co-culture initiation. Without priming of MSCs, however, there was no net movement of T cells toward the MSCs. Therefore, MSCs promote the migration of T cells only after MSCs having been exposed to proinflammatory cytokines.

To examine the role of various cytokines in enabling MSCs to attract T cells, MSCs were pretreated with various combinations of recombinant cytokines and the resultant migration of pre-activated T cells in co-cultures was observed. This analysis indicated that the same T cell cytokine pairs (i.e., IFNγ and TNFα, IFNγ and IL-1α, or IFNγ and IL-1β) that had induced the immunosuppressive function of MSCs also caused them to attract T cells. Likewise, using antibody neutralization of specific cytokines, it was found that migration toward MSCs was prevented by anti-IFNγ alone, or by blocking TNFα, IL-1α and IL-1β as a threesome, identical to their effects on activated-splenocyte-supernatant-induced MSC suppression of T cell proliferation. Therefore, the cytokine-induced immunosuppressive function of MSCs is likely to depend on the migration of lymphocytes into proximity with MSCs, where NO levels are highest.

Example 5

Proinflammatory Cytokines Induce MSCs to Produce Chemokines that are Critical for Immunosuppression The robust migration of activated T cells toward cytokine-primed MSCs indicated that the MSCs secrete potent chemoattractants, such as chemokines. Accordingly, the production of leukocyte chemokines by MSCs cultured under various conditions was determined by assaying the supernatant. No significant chemokine production was observed for MSCs cultured alone without cytokines, corroborating the findings that MSCs in their innate form are unable to attract T cells. When co-cultured with anti-CD3-activated splenocytes, however, MSCs produced several chemokines in large amounts, including CXCL-9 (MIG) at 1.5 ng/ml (12 ng/ml in another experiment) and CXCL-10 (IP-10) at 50 ng/ml at a MSC:splenocyte ratio of 1:60. These are potent T cell-specific chemokines; it has been shown that concentrations of only 1 to 10 ng/ml of either chemokine alone drive significant chemotaxis in vitro (Loetscher, et al. (1998) *Eur. J. Immunol.* 28:3696-3705; Meyer, et al. (2001) *Eur. J. Immunol.* 31:2521-2527). The production of CXCL-9 and CXCL-10 was inhibited by antibody neutralization of IFNγ alone, or all three cytokines TNFα, IL-1α and IL-1β, similar to the effects on immunosuppression induction. Chemokine production was similarly induced by adding recombinant IFNγ and TNFα (20 ng/ml each) to MSCs alone, with TNFα again being interchangeable with IL-1α and IL-1β. Therefore, these cytokines are sufficient to induce MSC expression of chemokines, which are likely to be responsible for driving T cell chemotaxis toward MSCs. Thus, once they have migrated into close proximity with MSCs, activated T cells would be expected to secrete cytokines that induce the production of additional chemokines by the MSCs, thus creating a positive feedback loop to attract still more T cells to the vicinity of MSCs.

To systematically examine the chemokine expression profile of MSCs, the expression of 84 different genes encoding chemokines and their receptors was examined in MSCs treated with supernatant from naïve or anti-CD3-activated splenocytes. Total RNA was analyzed by real-time PCR using the Mouse Chemokines and Receptors $RT^2$ PROFILER™

PCR Array kit, and chemokine mRNA levels compared to that of β-actin (Table 1). The some human cytokine combination also induced similar chemkine production in human MSCs.

TABLE 1

| Gene Symbol | Naive Spln Sup | Activated Spln Sup | Fold Increase |
|---|---|---|---|
| Cxcl9 | 4 | 8,963,294 | 2,025,082 |
| Cxcl5 | 2 | 4,302,867 | 1,978,890 |
| Cxcl2 | 2 | 2,711,838 | 1,681,250 |
| Ccl7 | 0 | 24,269 | 1,111,786 |
| Cxcl10 | 111 | 19,719,159 | 177,864 |
| Cxcl1 | 47 | 5,170,437 | 110,278 |
| Ccl5 | 215 | 8,022,162 | 37,344 |
| Ccl2 | 3,252 | 11,653,869 | 3,584 |
| Cxcl11 | 5 | 17,370 | 3,534 |
| Ccrl2 | 110 | 56,765 | 518 |
| Ccl17 | 294 | 23,212 | 79 |
| Cx3cl1 | 69,309 | 2,349,699 | 34 |
| Cmkor1 | 32,965 | 617,300 | 19 |
| Ccl8 | 628 | 10,070 | 16 |
| Ccl9 | 182 | 2,193 | 12 |
| Ccr9 | 999 | 3,860 | 4 |
| Cxcl13 | 19,067 | 48,073 | 3 |
| Cxcr6 | 4,943 | 7,516 | 2 |
| Cmklr1 | 49,839 | 47,340 | 1 |
| Ccbp2 | 0 | 9,015 | N/A |
| Actb | 10,000,000 | 10,000,000 | 1 |

MSCs ($1 \times 10^6$/T-25 flask in 5 ml) were stimulated with supernatant (sup) from naïve or activated splenocytes (Spln) as 50% of the culture medium for 12 hours. The gene expression of chemokines and chemokine receptors was assayed by real-time PCR using the Mouse Chemokines and Receptors RT² PROFILER™ PCR Array kit.
Actb (β-Actin) defined as $1 \times 10^7$ Units.

It was found that, except for low levels of CX3CL-1 (fractalkine) and CXCL13 (Chemokine (C—X—C) ligand 13, BCA-1), mRNA levels in MSCs exposed to naïve splenocyte supernatant were insignificant. Strikingly, treatment of MSCs with activated splenocyte supernatant resulted in a more than one million-fold increase in some chemokines, such as CXCL2 (Chemokine (C—X—C) ligand 2, Groβ), CXCL5 (Chemokine (C—C) ligand 5, RANTES), CXCL9 (Chemokine (C—X—C) ligand 9, MIG), CXCL10 (Chemokine (C—X—C) ligand 10, IP-10) and CCL7 (Chemokine (C—C) ligand 7, MCP-3). In absolute terms, some chemokines reached the same level of expression as β-actin, or even higher. For example, CXCL10 showed twice the mRNA copy number as β-actin. The chemokines that were most highly induced are extremely potent inducers of leukocyte chemotaxis and are likely to play an important role in immunosuppression by MSCs. In fact, it was observed that antibody blockade of CXCR3, a receptor for the T cell chemokines CXCL9, CXCL10 and CXCL11 (Lazzeri & Romagnani, (2005) Curr. Drug Targets Immune Endocr. Metabol. Disord. 5:109-118), which were all highly induced in MSCs, inhibited the chemotaxis of T cell blasts toward MSCs and reverted the suppression of their proliferation.

To directly examine the chemotaxis-driving capacity of proinflammatory cytokine-induced MSC supernatant, the CHEMOTX Chemotaxis System (NeuroProbe) was employed. This system is composed of upper and lower chambers separated by a polyvinylpyrrolidine-free polycarbonate membrane (5 µm pore size). Supernatant from MSC cultures was placed in the lower chambers and activated CD4⁺ or CD8⁺ T cell blasts were added to the upper chambers in the presence of IL-2. Chemotaxis was quantified after 3 hours. It was found that dramatic chemotaxis by both CD4⁺ and CD8⁺ T cells occurred in response to culture supernatant from MSCs treated with IFNγ plus TNFα or with IFNγ plus IL-1. Similar results were obtained with supernatant from MSCs treated with medium conditioned by activated splenocytes. In contrast, negative control supernatants from untreated MSCs or activated splenocytes alone were non-chemotactic, as was the direct addition of IFNγ plus TNFα without MSCs. Importantly, this chemotactic activity could be blocked by antibodies against CXCR3 and CCR5, two of the most important T cell-specific chemokine receptors, especially when both antibodies were added together. In addition to recruiting T cells, cytokine-activated MSCs also attracted bone marrow-derived dendritic cells, macrophages, and B cells.

The CHEMOTX system was also used to examine the role of chemotaxis in the inhibition of T cell proliferation. In this assay, MSCs were added to the lower wells, with or without addition of IFNγ plus TNFα, and T cell blasts (with IL-2) were added to the upper wells. In this set-up, chemokines produced by MSCs in the lower wells should induce T cell migration through the membrane and into the lower wells, where NO produced by MSCs could thus inhibit their proliferation. After a 3-hour incubation, both the upper and lower wells were pulsed with $^3$H-thymidine for an additional 6 hours and cells in both wells harvested for determination of proliferation. Proliferation levels of both CD4⁺ and CD8⁺ T cell blasts were significantly inhibited by MSCs in the presence of IFNγ and TNFα. Again, blocking antibodies against the T cell chemokine receptors, CXCR3 and CCR5, significantly reversed this effect. These data further indicate that T cell chemotaxis is critical in MSC-mediated immunosuppression.

Taken together, these results indicate that when MSCs are exposed to pro-inflammatory cytokines during an immune reaction, they produce large amounts of several chemokines, especially those specific for T cells, which thus attract T cells into close proximity to MSCs, where high concentrations of NO act to suppress T cell function.

Example 6

Figure 2:
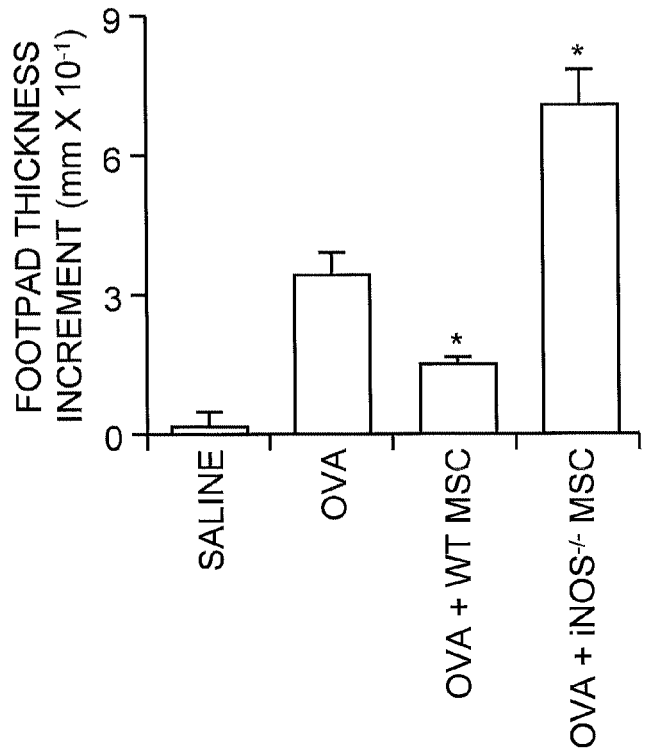
FIG. 2 is a graph showing that iNOS-Deficient MSCs Boost DTH. C57BL/6 mice were immunized with OVA in complete Freund's adjuvant by tail base injection. Mice were challenged in the footpad with 200 μg aggregated OVA administered with or without wild-type or $iNOS^{-/-}$ MSCs ($2.5 \times 10^5$ cells) on day 7. Footpad thickness increment was determined after 24 hours as a measure of DTH. Data shown are means±SD of a representative of three experiments. * p<0.005 vs. OVA alone.

Prevention of Delayed-Type Hypersensitivity (DTH) and Graft-Versus-Host Disease (GvHD) by MSCs is Dependent on Inflammatory Cytokines and NO Production It has now been shown that iNOS-deficient MSCs are incapable of inhibiting T cell function. However, iNOS-deficient MSCs do produce chemokines, suggesting that chemokine production by MSCs in response to cytokines is independent of NO. Therefore, it was expected that iNOS-deficient MSCs at a site of inflammation would attract T cells and thus promote immune reactions. To demonstrate this effect, mice were injected in the footpad with OVA alone or OVA and MSCs from iNOS-deficient or wild-type mice. The mice were then challenged in the footpad with OVA and the resultant DTH response measured by footpad swelling. The results of this analysis indicated that administration of wild-type MSCs resulted in reduced inflammation in the DTH response. In sharp contrast, iNOS-deficient MSCs not only did not reduce inflammation, but also actually enhanced the DTH response in comparison to challenged mice not injected with MSCs (FIG. 2). Histological analysis of the footpads showed reduced indicators of inflammation in skin from animals co-injected with wild-type MSCs, while those co-injected with iNOS$^{-/-}$ MSCs had increased fluid and leukocyte infiltration at the site of inflammation. This experiment not only demonstrates the requirement for NO in the suppression of an immune response, but also shows that, in the absence of NO production, MSC-mediated chemotaxis enhances inflammation, and could be used to boost local immune responses such as to promote the efficacy of vaccines or provoke effective immune responses to tumors using inhibitors to iNOS and IDO.

Figure 3:
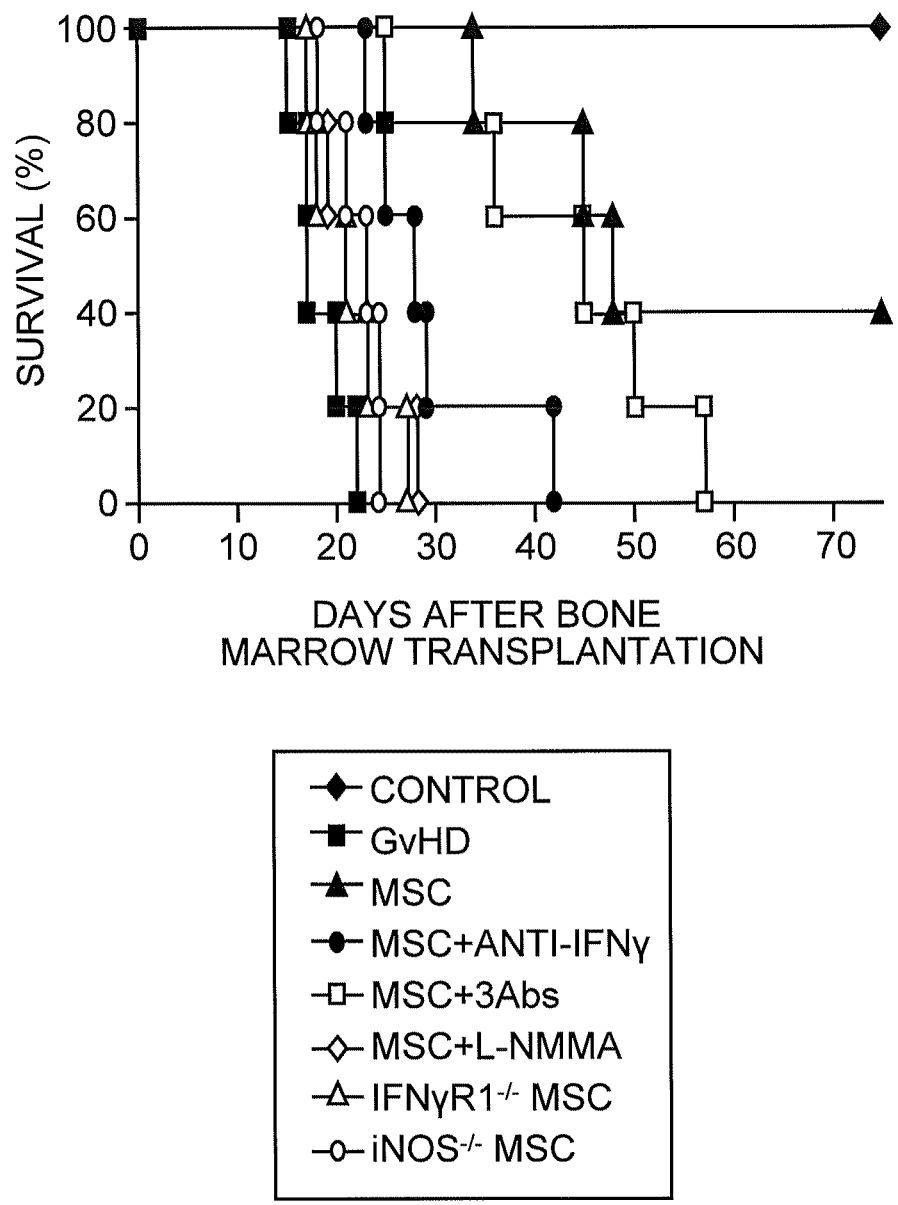
FIG. 3 is a graph showing that MSCs Prevent GvHD in a Manner Dependent on Inflammatory Cytokines and NO. Recipient mice (C57BL/6×C3H, F1) were lethally irradiated and injected i.v. with C57BL/6 bone marrow cells plus splenocytes. On days 3 and 7 after bone marrow transplantation, recipients were administered with the indicated MSCs. For some wild-type MSC groups, L-NMMA, anti-IFNγ or a 3-antibody cocktail against TNFα, IL-1α, and IL-1β (3 Abs) were injected i.p. Survival was monitored daily for 12 weeks.

One of the striking effects of immunosuppression by MSCs is the ability to suppress graft-versus-host disease (GvHD) (Le Blanc, et al. (2004) supra; Le Blanc & Ringden (2006) supra). To investigate whether cytokine-induced NO production by MSC results in immunosuppression in vivo, $5 \times 10^6$ nucleated bone marrow cells and $5 \times 10^6$ splenocytes from C57BL/6 mice were injected into lethally irradiated F1 (C57BL/6×C3H) mice to established the mouse GvHD model. All recipient positive-control mice developed extensive GvHD (wasting, ruffled hair, and hunched back) between days 15 and 22, while the negative controls that received syngeneic F1 bone marrow were unaffected. When F1 mice were treated with MSCs ($0.5 \times 10^6$ cells derived from donor mice injected i.v. on days 3 and 7) after bone marrow transplantation, there was significant protection from GvHD; all MSC-treated mice survived for at least 33 days and some for more than 75 days. In contrast, F1 mice treated with MSCs derived from iNOS$^{-/-}$ or IFNγR1$^{-/-}$ mice were not protected, as their survival was not different from untreated positive controls (FIG. 3). This lack of protection by MSCs deficient in IFNγR1 or iNOS indicates that IFNγ and NO production are essential for MSC-mediated immunosuppression in vivo.

Since in vitro results indicated that IFNγ acts together with either one of the three cytokines, TNFα, IL-1α or IL-1β to induce the immunosuppressive function of MSCs, the role of these cytokines was examined in MSC-mediated protection from GvHD. Mice were injected with neutralizing antibodies against these cytokines or L-NMMA for 7 days after wild-type MSC infusion, and GvHD was allowed to develop. Both anti-IFNγ and L-NMMA caused significant reversal of MSC-mediated protection from GvHD (FIG. 3), while negative control mice showed no adverse effect in response to these treatments. The effect of a 3-antibody cocktail against TNFα, IL-1α and IL-1β was less dramatic, not reaching statistical significance (FIG. 3). This result further implicates IFNγ and NO production, but is equivocal for the other cytokines. It is important to recognize, however, that besides synergizing with IFNγ to induce immunosuppression by MSCs, TNFα and IL-1 are also important factors in the normal pathogenesis of GvHD. In fact, it has been reported that neutralization of either TNFα or IL-1 can lessen the severity of GvHD (Hattori, et al. (1998) *Blood* 91:4051-4055; McCarthy, et al. (1991) *Blood* 78:1915-1918). Therefore, it was somewhat expected that protection from GvHD was not reversed to a greater extent by these antibodies.

Histological examination of the severity of inflammation in various organs from these mice was also examined 14 days after bone marrow transplantation. The extent of observed leukocyte infiltration correlated well with the survival results; GvHD-induced mice showed increased numbers of lymphocytes in the liver, lungs, and skin, while they were nearly absent in those treated with MSCs. In addition, protection by MSC was almost completely reversed by anti-IFNγ and L-NMMA, while the 3-antibody cocktail against TNFα, IL-1α and IL-11 were less effective. Together, the findings from these GvHD experiments, as well as those from the DTH studies, clearly indicate a role for IFNγ and NO in MSC-mediated immunosuppression in vivo.

Example 7

Tumor-Derived MSC-Like Lymphoma Stromal Cells are Immunosuppressive

Since the tumor cells in lymphoma are not adherent, it is possible to isolate tumor stromal cells from lymphomas developed in p53+/− mice. It was observed that these cells can be passaged in vitro and can be differentiated into adipocytes and osteoblast-like cells. Interestingly, like bone marrow derived MSCs, the stromal cells are also immunosuppressive and can effectively inhibit the proliferation of ant-CD3-activated splenocytes. This immunosuppressive effect was also dependent on IFNγ and NO, since ant-IFNγ and iNOS inhibitors could reverse the immunosuppressive effect.

Example 8

Figure 4:
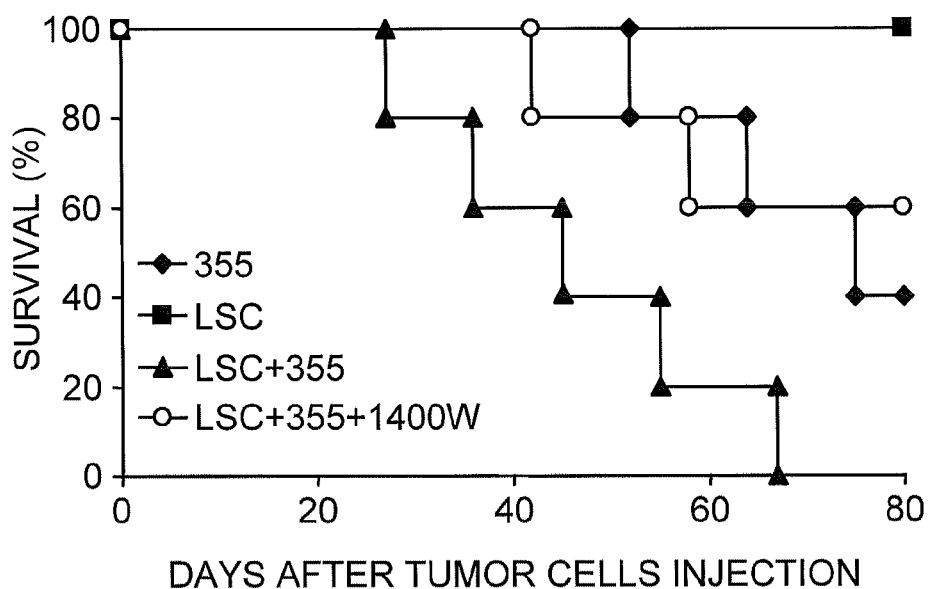
FIG. 4 is a graph showing that lymphoma stromal cells (LSCs) promote lymphoma development in a NO-dependent manner. 355 B-cell lymphoma cell line (C3H-gld/gld background, $0.5 \times 10^6$ cells/mouse) was co-injected with gld/gld mice-derived lymphoma stromal cells (C3H background, P5, $0.25 \times 10^6$ cells/mouse) by tail-vein i.v. on day 0.1400 W (NOS inhibitor, 0.1 mg/mouse) was injected on day 0, 2, 4, 8, 12, 16, 20, 24, and 28 by i.p. Mice survival was recorded when mice were moribund.

Lymphoma Stromal Cells (LSCs) Promote Lymphoma Development in a NO-Dependent Manner To examine the effect of lymphoma stromal cells on tumor growth, 355 B-cell lymphoma cell line (C3H-gld/gld background, $0.5 \times 10^6$ cells/mouse) was co-injected with gld/gld mice-derived lymphoma stromal cells (C3H background, P5, $0.25 \times 10^6$ cells/mouse). It was observed that co-injection of stromal cells significantly enhanced the mortality. Interestingly, administration of 1400 W (NOS inhibitor, 0.1 mg/mouse on day 0, 2, 4, 8, 12, 16, 20, 24, and 28) significantly reverted the effect (FIG. 4). Therefore, the tumor stromal cells could significantly promote tumor growth.

Example 9

Combination of NOS Inhibitor with IFNγ Promotes Mouse Melanoma Therapy

Figure 5:
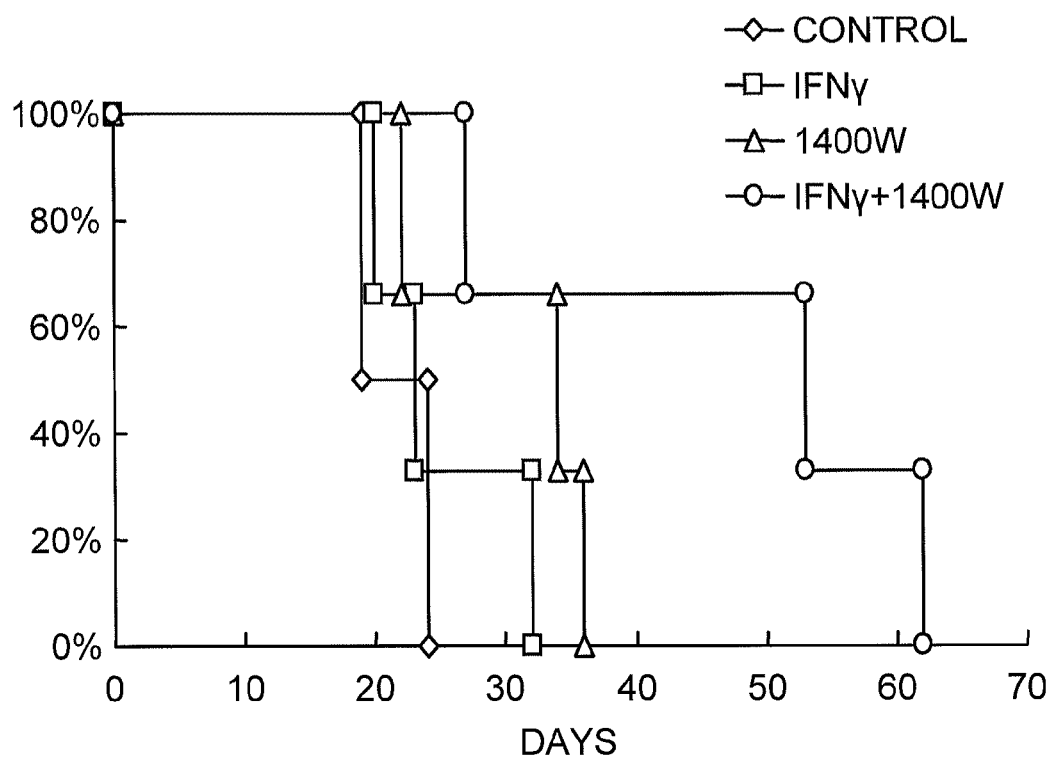
FIG. 5 is a graph showing that the combination of NOS inhibitor with IFNγ promotes mouse melanoma therapy. B16-F0 melanoma cells were injected into C57BL/6 mice on day 0 by i.v. ($0.5 \times 10^6$ cells/mouse). IFNγ (250 ng/mouse) and 1400 W (NOS inhibitor, 0.1 mg/mouse) were administrated by i.p. injection on day 4, 8, 12, 16, 20. Mice survival was recorded when mice were moribund.

To test the role of tumor stromal cell-produced NO on tumor immunotherapy, B16-F0 melanoma cells were injected into C57BL/6 mice on day 0 ($0.5 \times 10^6$ cells/mouse). IFNγ (250 ng/mouse) or 1400 W (NOS inhibitor, 0.1 mg/mouse) were administrated by i.p. injection on day 4, 8, 12, 16, 20. Mice survival was recorded when mice were moribund. It was observed that the combined therapy dramatically promoted mouse survival (FIG. 5). Thus, IFNγ has dual roles in tumor development; one is to prevent tumor development by producing some angiostatic factors or blocking some angiogenesis factor production, the other is to induce immunosuppression by tumor stromal or other environmental cells through producing factors like NO, IDO, or PGE2. Thus, inhibition of one or more of NO, IDO or PGE2 can dramatically enhance cancer treatment. Therefore, when immunotherapies such as those based on cytokines, vaccination, antibodies, dendritic cells, or T cells, are used to treat cancer, the tumor stromal cells might be responsible for the inability of these treatment to completely eradicate tumors in most cases. The combined used of inhibitors to iNOS and IDO with immunotherapies could provide effective ways to eradicate tumors.

What is claimed is:

1. A kit for attenuating an immune response mediated by activated T-cells in a subject in need thereof comprising
   (a) a pharmaceutically acceptable carrier selected from the group consisting of phosphate-buffered saline, physiological saline, 5% aqueous dextrose, and a mixture thereof;
   (b) a population of stem cells as the sole cell source within the kit consisting of cloned mesenchymal stem cells;
   (c) isolated interferon gamma;
   (d) isolated interleukin-1 alpha, interleukin-1 beta or tumor necrosis factor alpha; and
   (e) instructions for using the kit so that an immune response mediated by activated T-cells is attenuated.

2. The kit of claim 1, whereby the administration of a combination of (a), (b), (c) and (d) to a subject in need thereof achieves immunosuppression.

3. The kit of claim 1, wherein the instruction provides for administration of (a), (b), (c) and (d) to a subject in need thereof for achieving immunosuppression.

4. A kit for attenuating an immune response mediated by activated T-cells in a subject in need thereof comprising
   (a) a pharmaceutically acceptable carrier selected from the group of phosphate-buffered saline, physiological saline, 5% aqueous dextrose and a mixture thereof;
   (b) a population of stem cells as the sole cell source within the kit consisting of cloned mesenchymal stem cells;
   (c) isolated interferon gamma;
   (d) isolated interleukin-1 alpha, or interleukin-1 beta; and
   (e) instructions for using the kit so that an immune response mediated by activated T-cells is attenuated.

5. The kit of claim 4, wherein the instruction provides for administration of (a), (b), (c) and (d) to a subject in need thereof for achieving immunosuppression.

* * * * *